(12) United States Patent
Karapetyan

(10) Patent No.: US 6,996,846 B1
(45) Date of Patent: Feb. 14, 2006

(54) VISOR-TYPE FACE SHIELD FOR DENTIST

(76) Inventor: Armen Karapetyan, 1935 N. Van Ness Ave., Los Angeles, CA (US) 90068

( * ) Notice: Subject to any disclaimer, the term of this patent is extended or adjusted under 35 U.S.C. 154(b) by 0 days.

(21) Appl. No.: 11/143,520

(22) Filed: Jun. 2, 2005

(51) Int. Cl.
  A41D 13/11 (2006.01)
  A61F 9/04 (2006.01)
(52) U.S. Cl. .............................. 2/9; 2/10; 2/173; 2/206
(58) Field of Classification Search .................. 2/206, 2/8, 9, 10, 424, 453, 437, 436, 6.5, 5, 173, 2/169, 15, 422; 128/207.12, 201.24, 206.19, 128/206.15
See application file for complete search history.

(56) References Cited

U.S. PATENT DOCUMENTS

| | | | | |
|---|---|---|---|---|
| 2,631,286 A * | 3/1953 | Bowers | ............................. | 2/8 |
| 3,137,005 A * | 6/1964 | Herbine et al. | .................. | 2/10 |
| 3,214,768 A * | 11/1965 | Bohner | ............................. | 2/10 |
| 3,555,562 A * | 1/1971 | Patton, Jr. | ......................... | 2/10 |
| 4,673,431 A * | 6/1987 | Bricmont | ..................... | 75/694 |
| 4,694,507 A * | 9/1987 | Owen | ................................ | 2/8 |
| 4,701,965 A * | 10/1987 | Landis | .......................... | 2/428 |
| 4,726,074 A * | 2/1988 | Baclit et al. | ..................... | 2/10 |
| 4,852,186 A * | 8/1989 | Landis | ............................... | 2/9 |
| 4,853,974 A * | 8/1989 | Olim | ................................ | 2/9 |
| 4,937,879 A * | 7/1990 | Hall et al. | .......................... | 2/8 |
| 4,975,981 A * | 12/1990 | Ray | ................................. | 2/10 |
| 5,088,114 A * | 2/1992 | Salce et al. | .......................... | 2/9 |
| 5,105,475 A * | 4/1992 | Lynd et al. | ....................... | 2/10 |
| 5,469,229 A * | 11/1995 | Greenbaum | ................... | 351/44 |
| 5,647,060 A * | 7/1997 | Lee | .................................... | 2/9 |
| 5,692,522 A * | 12/1997 | Landis | ........................ | 128/857 |
| 5,765,223 A * | 6/1998 | McCausland | ....................... | 2/9 |
| 5,843,643 A | 12/1998 | Ratner | | |
| 5,956,760 A * | 9/1999 | Wine et al. | ........................ | 2/9 |
| 5,966,738 A * | 10/1999 | Wang Lee | ....................... | 2/10 |
| 5,991,072 A * | 11/1999 | Solyntjes et al. | ........... | 359/361 |
| 6,016,808 A * | 1/2000 | Landis | ......................... | 128/857 |
| 6,026,511 A * | 2/2000 | Baumann et al. | .................. | 2/9 |
| 6,250,299 B1 * | 6/2001 | Danisch et al. | ......... | 128/201.25 |
| D456,568 S * | 4/2002 | Ouellet | ...................... | D29/105 |
| 6,378,133 B1 * | 4/2002 | Daikuzono | ......................... | 2/9 |
| D458,713 S * | 6/2002 | Cheng | ....................... | D29/110 |
| 6,457,180 B1 * | 10/2002 | Jung | ............................... | 2/12 |
| 6,536,045 B1 * | 3/2003 | Wilson et al. | .................... | 2/15 |

* cited by examiner

Primary Examiner—John J. Calvert
Assistant Examiner—Richale L. Haney

(57) ABSTRACT

An improved visor-type face shield for dentist includes a visor portion and a shield portion coupled to each other by a first pivotable connecting means and second pivotable connecting means. The visor portion comprises a visor assembly, including a visor member and a forehead member, a visor first extension, a visor second extension, and a band, which is coupled with the first and visor second extensions by the band first connection means and band second connection means respectively. The shield portion includes a face shielding means comprising a rest extended from the face shield inner surface, a shield lower portion, a shield upper portion, a shield first connecting means of the first pivotable connecting means, and a shield second connecting means of the second pivotable connecting means. The face shielding means has the curved configuration forming some kind of semi-circular shape or the like, and the lower portion of the face shielding means is bent below the dentist's chin while the upper portion of the face shielding means is bent over the dentist's head.

8 Claims, 4 Drawing Sheets

VISOR-TYPE FACE SHIELD FOR DENTIST

FIELD OF THE INVENTION

This invention relates to the face shields as the face and eye protection devices, and more particularly to a plastic mask for use by the dentists (or e.g. surgeons and the others who may be contaminated with germs and viruses of their patients and customers or may contaminate them during, for example, dental procedure).

BACKGROUND OF THE INVENTION

Various types of face shields are known in the art, many of which are designed to protect the wearer against various occupational hazards. Such face shields are generally comprised of multi-components, such as a clear viewing/shield portion affixed to a helmet or visor unit and are generally fabricated of relatively thick, impact-resistant plastic. There are generally known and well described two preferred methods for fabricating a face shield with acceptable optical clarity. In the first method, the face shield may be injection molded in a mold that has a highly polished surface. Such processes generally require that the molded part have a thickness in excess of 0.040 inch (1.02 mm) to achieve reasonable polymer flow into the mold. Other than the thickness of the part, which is acceptable for most applications, this method produces very high quality precision parts of any desired configuration. In another method, a blank may be taken from an optically polished flat polymer sheet (the sheet is polished usually by pressing between two platens) and formed in a curved piece (i.e. cylindrical, not spherical) by heating the blank beyond its glass transition temperature and applying force in the direction of the desired curve. This method generally retains the optics of the original polished sheet, but is only suitable for simple curved pieces and cannot be utilized where the desired piece has a complex configuration. It is understandable, that there is a need in the medical profession (the term "medical" as used herein is intended to encompass the medical, dental and related professions) for a lightweight, preferably disposable, face shield to protect the medical professional from splattered body fluids so as to avoid the possibility of contamination therefrom. While certainly many of the heretofore known goggles and face shields might serve this purpose, such products tend to be bulkier and heavier than is desired by the medical professional, for example, such as dentists, and are costly.

Use of face shields has grown substantially in dental and medical professions, in response to the spread of AIDS and like infectious diseases, to prevent infection from body fluid splatter. It is well known, that the face shields are moistly supported on a wearer's head by a head band or head visor, with the face shield generally attached to the head band or visor such that the face shield is positioned in front of the wearer's face. Usually, the face shield is suspended directly from the edge or brim of a head worn visor to provide protection to a wearer's face. A frequent problem experienced by users of face shields is that currently known face shield devices are uncomfortable to wear, particularly for extended periods of time. Wearers must frequently reposition the face shield in order to minimize discomfort. Face shield devices which rely on entirely hard head bands tend to cause perspiration under the band or entirely hard strap, causing additional discomfort. Further, dentists, physicians, and other persons who rely shields on their face frequently have both hands occupied in difficult or complex medical procedures, and cannot free their hands to positionally adjust the face shield apparatus to reduce discomfort.

Another known deficiency common to conventional face shield devices is that the face shields are not readily detachable from the devices. Face shield device used in the medical and dental professions must be exchanged between treatment of each patient to avoid cross-infection or cross-contamination of patients. Many currently used face shield devices do not provide for easy removal or interchange of face shields or non-expensive face shield devices, so that contaminated face shields can be sterilized or disposed.

One more common problem inherent to many conventional face shield devices is that the face shields cannot undergo pivotal adjustment while on the wearer's head, or pivotal adjustment is difficult to make while the face shield is being worn.

Accordingly, there is a need for a face shield apparatus which is comfortable to wear, which is light weight, which provides for quick and easy detachment and re-attachment of face shields, and which provides for quick and easy pivotal adjustment of face shields while on the wearer's head. The present invention satisfies these needs, as well as others, and generally overcomes the deficiencies found in prior devices.

A face shield device attachable to the spectacles is described in the U.S. Pat. No. 4,843,643. Generally, this device comprises two small metallic bars each L-shaped and associated by means of an end portion thereof with one of the two temples of a pair of spectacles. The coupling is provided by means of rings of an elastic material, each whereof embraces a portion of a bar and of a temple arranged mutually side by side. The two bars thus associated with the spectacles are provided with two ends in front of said spectacles and parallel thereto, so that each is insertable in the opposite end of a hole which longitudinally traverses a monolithic cross supporting member, essentially parallelepipedal in shape. The monolithic cross member is longitudinally traversed by two vertical millings of grooves, one whereof extends in transverse cross section from the hole to the upper surface, the other one extending, again in transverse cross section, from a narrow central portion to a lower surface. The millings are the support and insertion seat for an upper portion of a rectangular shield or screen in transparent material and having antifogging surfaces, and are intended to allow a certain transverse elasticity to the monolithic element so as to provide both the friction for the rotation thereof about the center of the hole and the interchangeability of the shield. Thus, the visor is adapted to spectacles of all widths, since it is sufficient for this purpose to insert more or less deeply the ends in the hole.

This device is inconvenient considering that not all dentists (surgeons) wear regular spectacles (eye glasses with optical lenses) for vision correction, and second, the dentists who does not wear the eye glasses have to use the eye glasses frame (with plane glass/no optic lenses/) or eye glasses frame without any plane glass or lenses in order to provide the support for shield, that for most people not using regular spectacles is inconvenient and uncomfortable. Also, the use of the surgical mask surrounding the dentist's nose and mouth is preferably required with such shield. However, wearing such masks is hot and uncomfortable too. Putting the masks on and removing them are time consuming and often difficult. It is known, that surgical masks cause the wearer to re-inhale exhaled breath causing the $CO_2$ content of the blood to rise, and the result of this may be increased heart and respiration rates and higher body temperatures and perspiration.

A face shield apparatus having a frame assembly instead of the spectacles is described in U.S. Pat. No. 5,692,522. This face shield apparatus includes a frame assembly and the detachable and replaceable face shield coupled thereto. The frame assembly generally comprises a pair of generally parallel, spaced apart side members which are joined to a front member, which is supported by the wearer's nose or forehead. Articulating tails are included on the frame side members. One or more posts are provided on the frame assembly which pivotally engage one or more sockets associated with the face shield and provide for pivotal adjustment of the face shield relative to the frame assembly.

This face shield apparatus is complex, inconvenient and not sufficiently reliable because of the presence of engaged posts and the mounting rod detachably coupled to face shield by means of a plurality of studs installed into corresponding holes in face shield. Also, the face shield apparatus is not reliable, because the weight of the shield portion (the shield with the frame portion located in the front of the dentist's face) is supposedly heavier than the weight of the rest of the frame portion (articulating tails and the appropriate side members with the pivotally engaged posts and sockets). This requires tighter coupling of the apparatus with the head of dentist (i.e. the construction of the frame does not provide reliable coupling of the apparatus to the dentist head).

Additionally, the shield's left and right sides are bended under "sharp" angle, that limits the dentist visibility in the "rib" areas. Another deficiency of this apparatus is that the dentist has to use the surgical mask with such face shield.

To avoid such deficiency of visibility limitation, the U.S. Pat. Nos. 6,016,808 and D375,583 disclose the face shield including semi-circular configuration of the shield. The face shield frame apparatus by the mentioned patents comprises a head worn frame assembly to which a face shield can be detachably coupled. The frame assembly includes a pair of generally parallel, spaced apart side members which are joined to a front member, which is supported by the wearer's nose or forehead. One or more receptacles are provided on the frame assembly which slidably engage one or more latch arms associated with the face shield support, or conversely, the receptacle may be attached to the face shield support and the latch arm attached to the frame assembly. The latch arm has a locking tab which fits within a slot on the receptacle to lock the latch arm to the receptacle when the latch arm is inserted into the receptacle. The latch arm can also be removed from the receptacle by depressing the locking tab so that it disengages from the slot.

The face shield apparatus by U.S. Pat. No. 6,016,808 has the same deficiency as the previous prior art, i.e. the mentioned face shield apparatus is not sufficiently reliable, because the weight of the shield portion (the shield with the frame portion located in the front of the dentist's face) is supposedly heavier than the weight of the rest portion of the frame portion (the side members, etc.). This requires tighter coupling of the apparatus with the head of dentist (e.g. the construction of the frame does not provide reliable coupling of the apparatus to the dentist head), and the face shield by U.S. Pat. No. D375,583 has the dentist's head and face protecting device coupling means providing not precise (tightened) adjustment considering the step-type size adjusting process instead of the evenness. Also, the dentist using either one of these shields has to use the surgical mask.

More reliable construction of the face shield device is described in the U.S. Pat. No. 4,701,965. The shield of this invention is supported by means of a band of a material such as polyethylene which is resiliently flexible. The center portion fits around the forehead of the wearer and extends around the sides of the head terminating in ends on either side which grip the head sufficiently strongly to hold the device in place without creating discomfort. Integral with and extending forwardly from the band, is a visor shaped in the manner of a conventional sun visor.

Also, the device generally includes studs projecting from the visor. A shield is detachably secured to visor. To facilitate the studs snapping into and out of the holes, radial slits are formed in the shield which provide prongs which engage under the studs. Thus, the shield may be snapped onto the visor or removed therefrom.

Particularly for dentistry, a filter of an orange plastic which filters ultraviolet or high wave-length the blue light is disposed across the shield at a level slightly below the nose. In normal use, the filter is out of the line of sight through the shield. it is known that dentists frequently use ultraviolet or blue light lamps (not shown) to cure plastic tooth-filling materials. By tilting the head upward and directing the eyes, the filter is interposed between the instrument emitting the ultraviolet light and the eyes of the wearer to protect against damage.

But, this device is complex and also does not provide reliable coupling with the dentist's head. Additionally, the dentist has to preferably use the surgical mask with such shield.

So, in all previously described prior art, the dentist (surgeon, person/wearer whose occupation is in the medical field) has to use the surgical mask (e.g. the masks of gauze, paper, etc.) surrounding the dentist's nose and mouth to prevent intercontamination of the doctor and patient.

The mask used for such purpose is shown and described in the U.S. Pat. No. 5,469,229. The protective eye shield by this invention is used together with the mask.

There are many known face shields of different constructions providing the possibility to avoid the surgical masks. For example, the one-piece protective face shield to protect against contamination from splattered body fluids is described in U.S. Pat. No. 5,088,114. This face shield has a configuration providing possibility to eliminate the surgical mask. The device includes a curved brow member which is adapted to substantially conform with and contact a wearer's forehead. The uppermost edge of the curved brow member is curved away from the wearer's forehead to avoid contact of the forehead with any sharp edges which might cause discomfort. A face shield body (also referred in the invention to as eye protective shield) extends first outwardly at surface, then downwardly from the curved brow member and is integral therewith. The face shield body is adapted to cover at least a portion of the wearer's face (i.e. at least the wearer's eyes) without contacting any part of the face below the forehead. When means for retaining the curved brow member against the wearer's forehead, such as elastic band, are affixed to the face shield. The face shield is fabricated as one-piece out of a transparent, optical grade, thermoplastic material.

The face shield body also comprises an upper viewing portion which is disposed in the wearer's viewing path. This viewing portion is bubble-shaped. The lower portion extends downwardly from the upper viewing portion, and more specifically, the lower portion at first extends outwardly slightly from the upper viewing portion, then downwardly, so as to create a deflecting point to direct exhaled air away from the upper viewing portion.

This device has a complex configuration that leads to high cost of manufacturing, and as result is expensive for dental offices. Also, such massive face shield is inconvenient, limits the dentist's breathing that is uncomfortable during dental procedure.

Thus, there is a great need in the art for the non-complex, non-expensive and convenient improved visor-type face shield for dentist eliminating the necessity of the surgical mask use, and which is comfortable to wear, which is light weight, which provides for quick and easy detachment and re-attachment of face shields, and which provides for quick and easy pivotal adjustment of face shields while on the dentist's head. The present invention satisfies these needs, as well as others, and generally overcomes the deficiencies found in prior art.

OBJECT AND ADVANTAGES OF THE INVENTION

Accordingly, several objects and advantages of the present invention are to provide a non-expensive visor-type face shield for dentist, providing reliable coupling of the improved face shield with the dentist's head and eliminating the necessity of the surgical mask use.

It is another object of the invention to provide a possibility of the maximum visibility with the wide vision angle.

It is still another object of the invention to provide a convenient face shield for dentist reliably preventing inter-contamination of the dentist and patient.

Still, further objects and advantages will become apparent from a consideration of the ensuing description accompanying drawings.

DESCRIPTION OF THE DRAWING

In order that the invention and the manner in which it is to be performed may be more clearly understood, embodiments thereof will be described by way of example with reference to the attached drawings, of which.

SUMMARY OF THE INVENTION

The known non-complex, non-expensive and convenient visor-type face shield for dentist do not provide possibility to eliminate the surgical mask use.

There is a great need in the art for the non-complex, non-expensive and convenient improved visor-type face shield for dentist eliminating the necessity of the surgical mask use, and which is comfortable to wear, which is light weight, which provides for quick and easy detachment and reattachment of face shields, and which provides for quick and easy pivotal adjustment of face shields while on the dentist's head. The present invention satisfies these needs, as well as others, and generally overcomes the deficiencies found in prior art.

An improved visor-type face shield for dentist includes a visor portion and a shield portion coupled to each other by a first pivotable connecting means and second pivotable connecting means. The visor portion comprises a visor assembly, including a visor member and a forehead member, a visor first extension, a visor second extension, and a band, which is coupled with the first and visor second extensions by the band first connection means and band second connection means respectively. The shield portion includes a face shielding means comprising a rest, a shield lower portion, a shield upper portion, a shield first connecting means of the first pivotable connecting means, and a shield second connecting means of the second pivotable connecting means. The rest is extended from the face shield inner surface and perpendicular to it. The face shielding means 25 has the curved (arcuate) configuration forming some kind of semi-circular shape (in transverse horizontal section) or the like. The lower portion of the face shielding means is bent below the dentist's chin (slightly "overlapping" the dentist's chin), and the upper portion of the face shielding means is bent over the dentist's head (slightly "overlapping" the dentist's head).

DESCRIPTION OF THE PREFERRED EMBODIMENTS

Herein the description of an improved visor-type face shield for dentist will be done in statics (as if the components of the improved device are suspended in the space) with the description of their relative coupling to each other. The description of the functional operations of the improved visor-type face shield for dentist will be done hereinafter.

Figure 1:
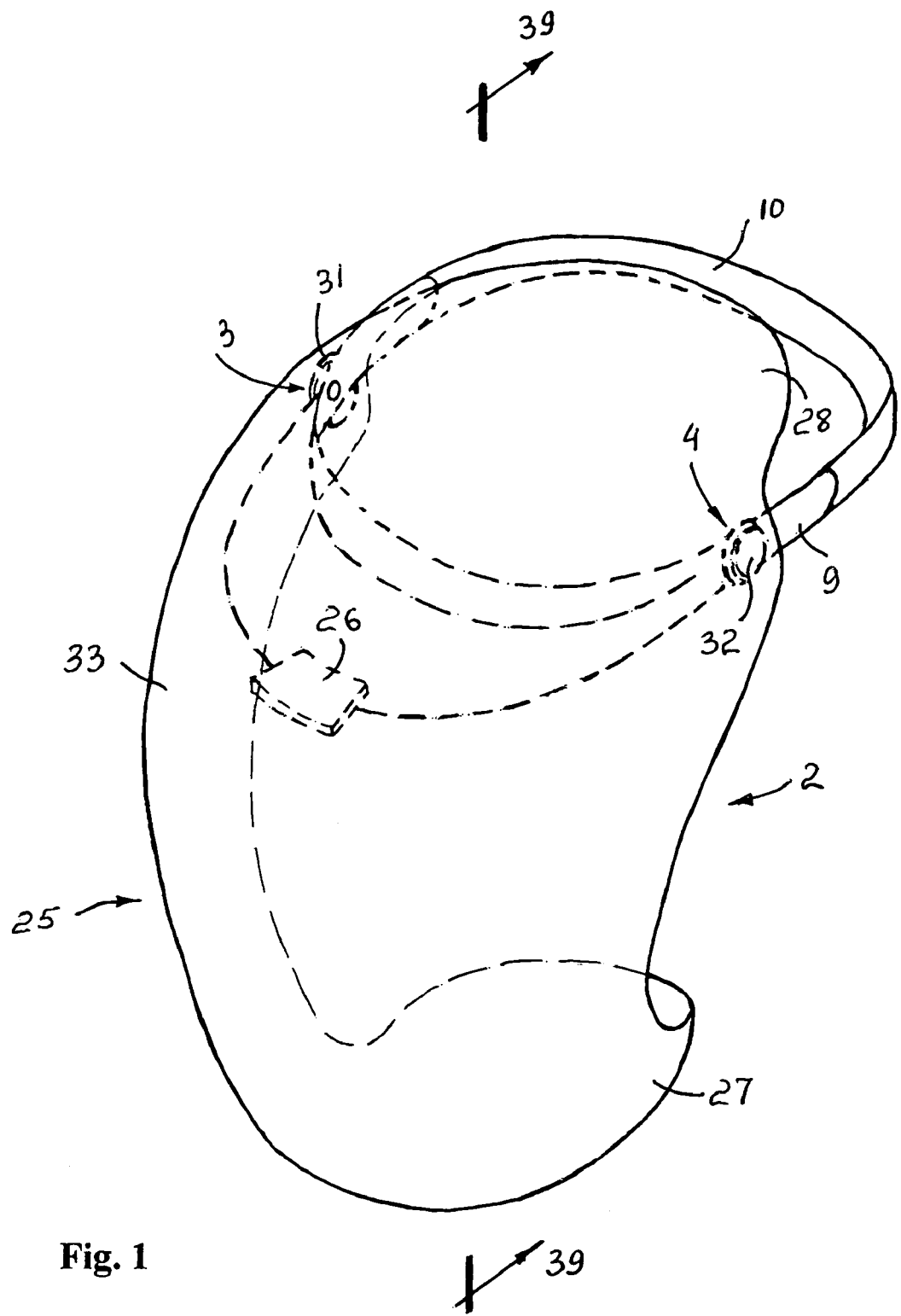
FIG. 1 is a simplified spatial view of the improved visor-type face shield for dentist.

An improved visor-type face shield (device) for dentist, referring to FIG. 1, includes a visor portion 1 and a shield portion 2 coupled to each other by a first pivotable connecting means 3 and second pivotable connecting means 4. The visor portion 1 comprises a visor assembly 5, including a visor member 6 and a forehead member 7, a visor first extension 8, a visor second extension 9, a visor first connecting means 29 of the first pivotable connecting means 3, a visor second connecting means 30 of the second pivotable connecting means 4, and a band 10, which is coupled with the first 8 and second 9 visor extensions by the band first connection means 11 and band second connection means 12 respectively. The visor member 5 and forehead member 6 can be made (e.g. molded, etc.) of one (e.g. entire, solid, etc.) piece of material, or can be made of two separate pieces connected to each other (e.g. glued, screwed, riveted, etc.). The same can be applicable to the visor first extension 8 and visor second extension 9, i.e. the first 8 and second 9 extensions can be appropriately extended from the visor assembly 5, or can be connected to the visor assembly 5, for example, by glue, screw(s), rivet(s), etc. The visor first 8 and second 9 extensions are preferably slightly springy. The band 10 can be made of any flexible material (e.g. such as reliable slightly hard fabric, etc.). The band first connection means 11 and band second connection means 12 can be, for instance, presented by the "Velcro" locks, where the first half 13 of the first "Velcro" lock (band first connection means 11) is appropriately attached to the outer side 17 of the visor first extension 8 at its free end 19, and the another (second) half 14 of the first "Velcro" lock is appropriately attached to the inner side 18 of the first end 15 of the band 10. The first half 20 of the second "Velcro" lock (band second connection means 12) is appropriately attached to the outer side 22 of the visor second extension 9 at its free end 24, and the another (second) half 21 of the second "Velcro" lock is appropriately attached to the inner side 18 of the second end 16 of the band 10. The connection of the first halves 13 and 20 of the respective first 11 and second 12 band connection means (hereinto "Velcro" locks) to the appropriate first 8 and second 9 visor extensions can be, for example, provided by the double side adhesive tape (not shown), etc.

Figure 2:
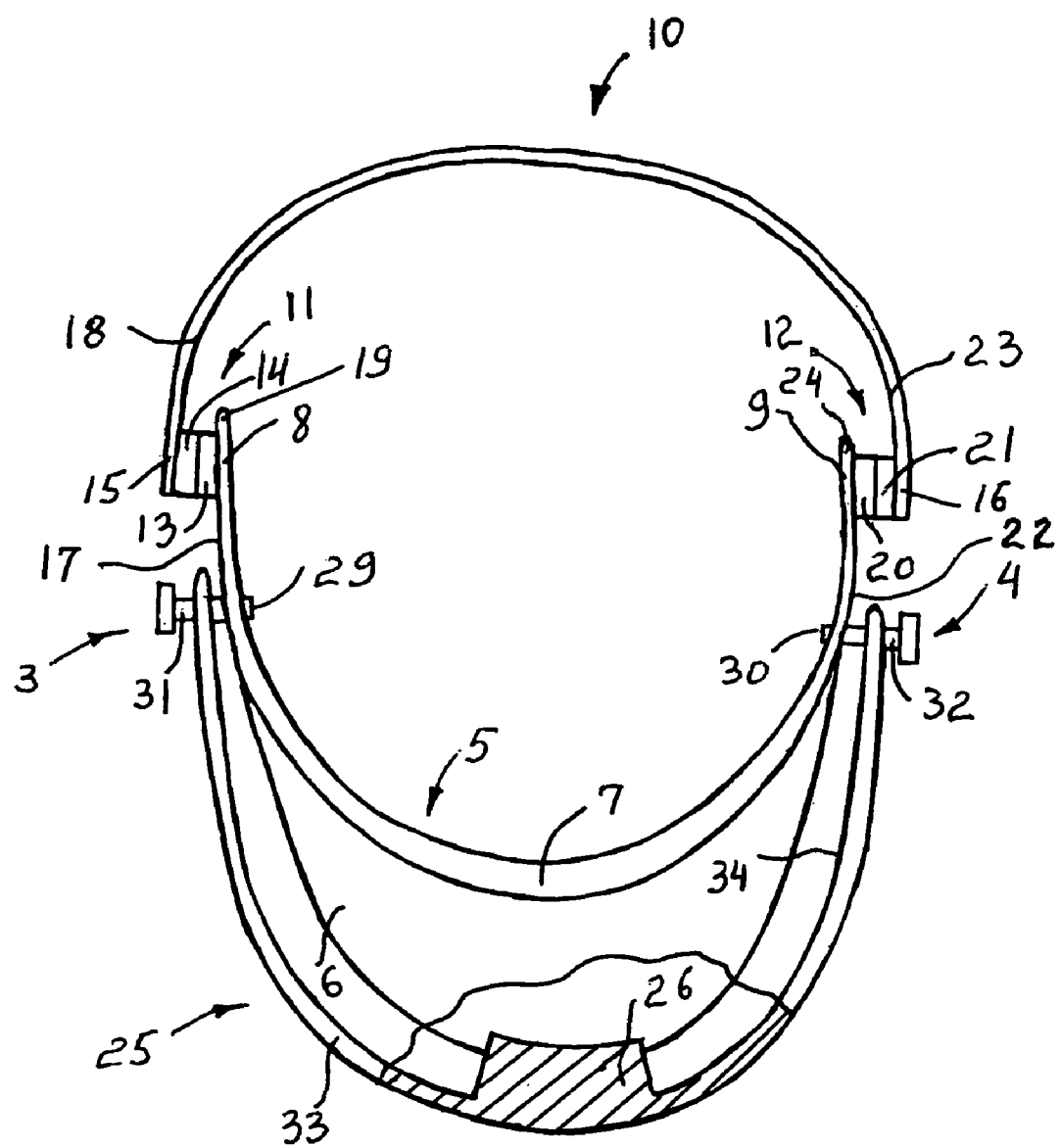
FIG. 2 is a simplified top view of the improved visor-type face shield for dentist.

The band first 11 and second 12 connection means are not limited by the described "Velcro" locks, and can be presented by any convenient and reliable type of the connection means, for example, by clamping locks (not shown) attached to the free ends 19 and 24 respectively of the first 8 and second 9 visor extensions, etc. (see also FIG. 2).

Figure 3A:
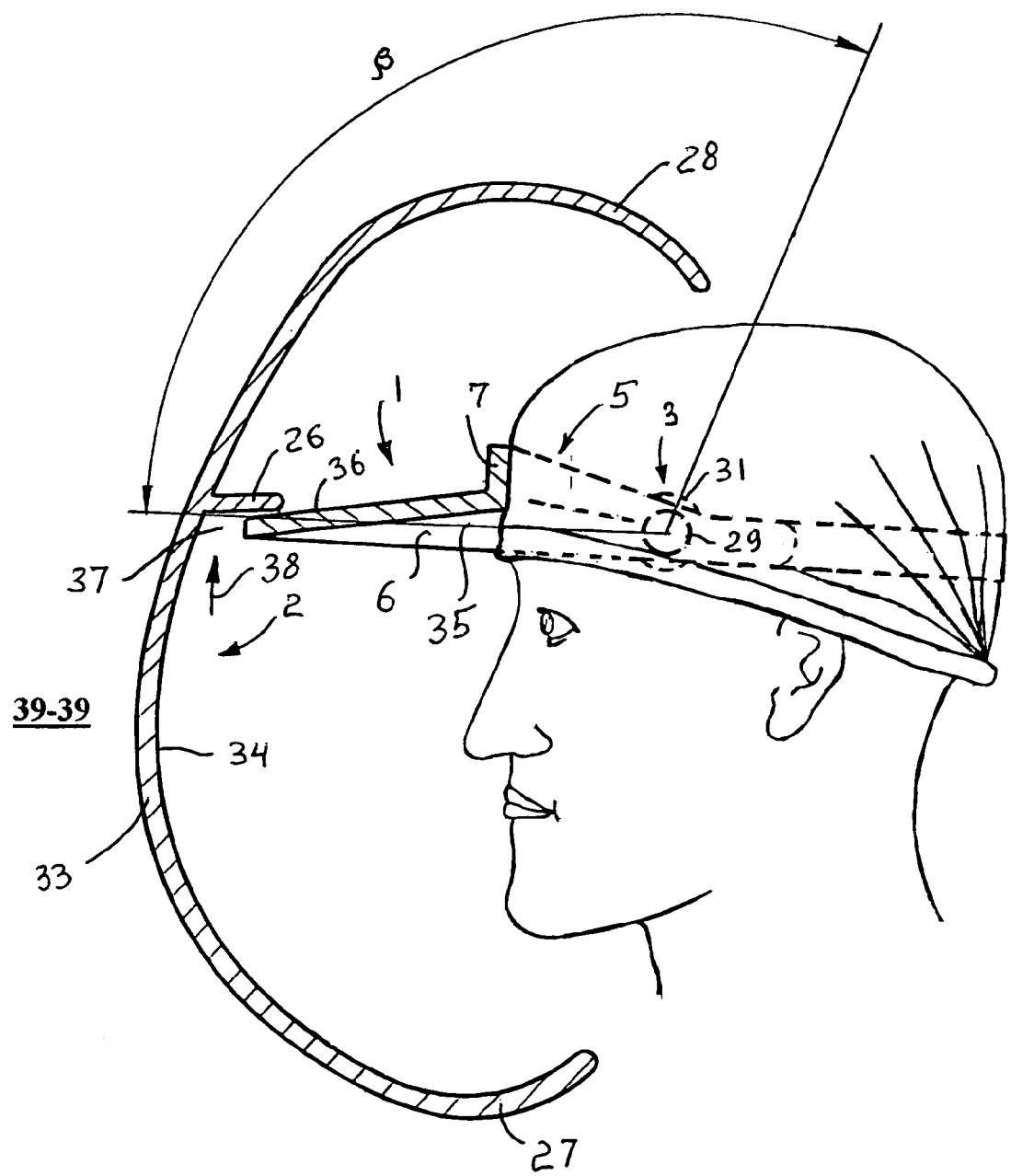
FIGS. 3a, 3b are the simplified cross-sectional side views of the improved visor-type face shield for dentist.
Figure 3B:
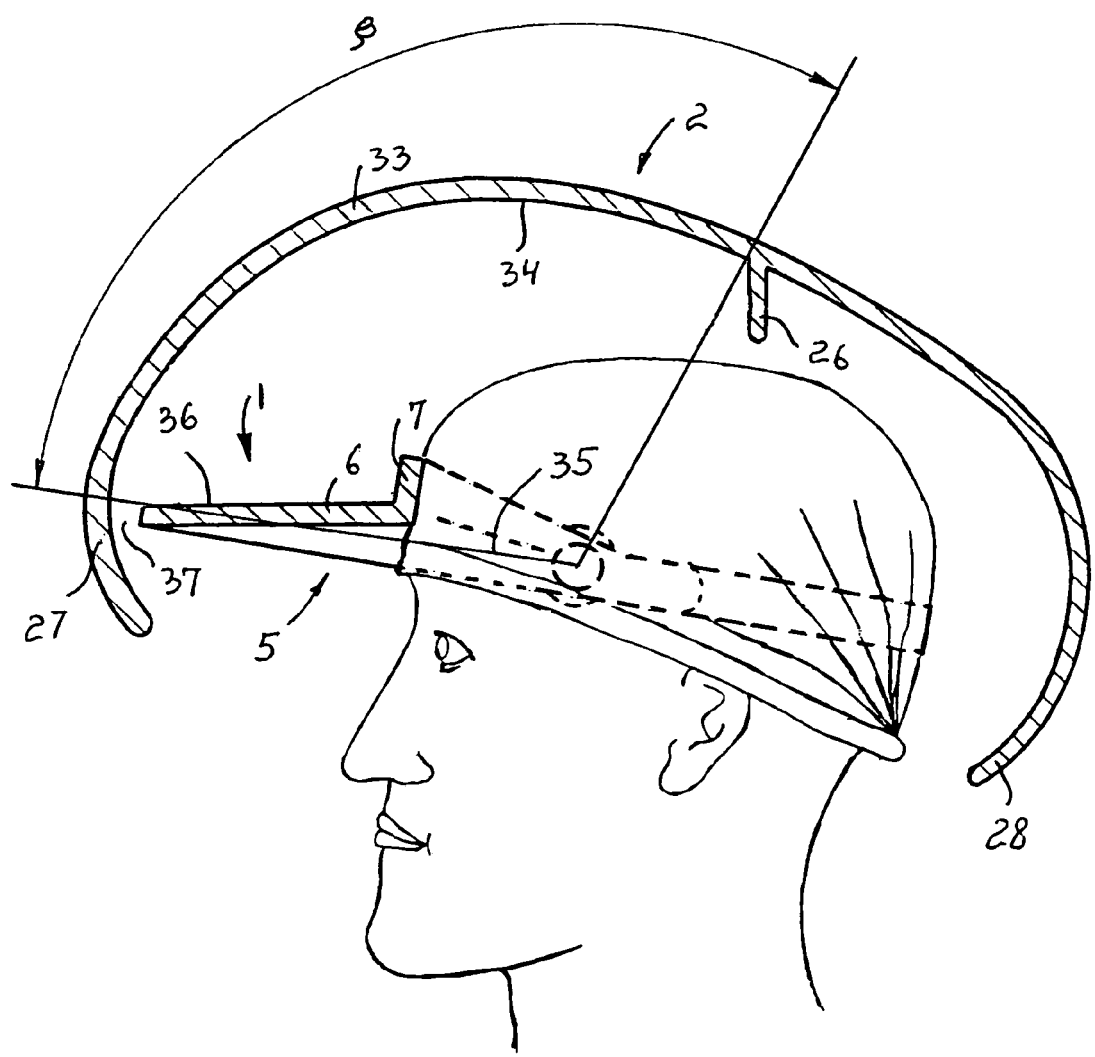

The shield portion 2 includes face shielding means 25 comprising a rest 26, a shield lower portion 27, a shield upper portion 28, a shield first connecting means 31 of the first pivotable connecting means 3, and a shield second connecting means 32 of the second pivotable connecting means 4. The rest 26 is perpendicularly extended from the inner surface 34 of the face shield 33. The rest 26 can be attached (not shown) to the face shield 33 (for example, can be glued to the inner surface 34 of the face shield 33, etc.). The rest 26 is located preferably in the middle area of the face shield inner surface 33 of the face shielding means 25, as it is shown in FIGS. 1, 3a, 3b. The rest 6 can be of any form, size and configuration and is not limited by description given hereinto. For instance, the rest 26 can be also presented by a plurality of short rests (not shown) instead of the single piece 26, as shown in FIGS. 1, 3a, 3b. The face shielding means 25 has the curved (arcuate) configuration forming some kind of semi-circular shape (in transverse horizontal section) or the like (for example, the parabolic (not shown), elliptic (not shown), exponential (not shown), etc. shapes can be used too). The lower portion 27 of the face shielding means 25 is bent below the dentist's chin (slightly "overlapping" the dentist's chin), as shown in FIG. 3a, and the upper portion 28 of the face shielding means 25 is bent over the dentist's head (slightly "over-lapping" the dentist's head), as shown in FIG. 3a. Such face shielding means configuration provides the maximal face protection and eliminates the use of the surgical mask. The face shielding means 25 can be of any configuration, e.g. can include only lower part comprising the rest 26 and the downward portion.

The shield first connecting means 31 of the first pivotable connecting means 3 is coupled with the visor first connecting means 29 of the first pivotable connecting means 3, and the shield second connecting means 32 of the second pivotable connecting means 4 is coupled with the visor second connecting means 30 of the second pivotable connecting means 4. The first 3 and second 4 pivotable connecting means can have any design providing possibility to rotate face shielding means 25 around horizontal axis 35, taking any positions between face shielding means 25 positions shown in FIG. 3a and FIG. 3b ("γ" can approximately be in the range of 0°–100°). The lowest position of the face shielding means 25 shown in FIG. 3a is corresponded to the moment when the rest 26 is leant on the upper surface 36 of the visor member 6. The first 3 and second 4 pivotable connecting means can be of any kind (e.g. it can be a clamping-type or clipping-type connecting means, fast screwing-type connecting means, locking-type connecting means, etc. and any other known reliable connecting means using any reliable connecting principles). The first 3 and second 4 pivotable connecting means can include the tightening means (not shown), providing the fixation of the face shielding means position relatively to the visor member 6 of the visor portion 1. The coupling of the shield portion 2 to the visor portion 1 can be provided by non-pivotable connecting means (not-shown). In this variant, the shield portion 2 can have detachable construction (for this way the both visor 1 and shield 2 portion can be separately disposable) or non-detachable construction (in such variant the entire device is disposalable).

As shown in FIG. 3a, the gap 37 provides the conventional ventilation of the space between dentist's face and inner surface 33 of the face shielding means 25. Such conventional ventilation through the gap 37 in the direction 38 provides the perspiration prevention, thereby providing clear visibility.

Although, the described shape of the shield portion 2 and/or face shielding means 25 can be subject to any modification (not shown), considering compliance with the necessity to conveniently cover the eyes, nose and mouth of the user (dentist).

The improved visor-type face shield (device) for dentist can be used as following. The user (dentist) may to put on the visor portion 1 first and later connect the shield portion 2 to the visor portion 1 or may put on the fully assembled device (the visor portion 1 and shield portion 2 coupled to each other). The either one of the coupling is provided by the first 3 and second 4 pivotable connecting means. When the dentists uses the fully assembled device (the visor portion 1 and shield portion 2 coupled to each other), he/she before to put it on can for convenience arrange the shield portion 2 position as shown in FIG. 3b, and then using the pivotable connecting means 3 and 4 to place the shield portion 2 in the position shown in FIG. 3a. The first 3 and second 4 pivotable connecting means also provide quick and easy pivotal adjustment of face shields while on the dentist's head.

Thus, the described invention presents the improved not expensive visor-type face shield for dentist.

All means, components, portions, members, etc. described herein can be of any reasonable geometrical forms and configurations, can be of any reasonable size, color, etc., and can be of any non-toxic material.

It should be understood that numerous modifications and variations of the present invention are possible in light of the above teachings and it is also understood that the above description discloses specific embodiments of the present invention and are for purposes of illustration only without any limitations. There may be other modifications and changes obvious to those of ordinary skill in the art which fall within the scope of the present invention and within scope of the appended claims, the invention may be practiced otherwise than as specifically described herein.

CONCLUSION, RAMIFICATION AND SCOPE

Accordingly the reader will see that, according to the invention, I have provided the improved visor-type face shield for dentist. The improved visor-type face shield for dentist has various possibilities, considering dental practice.

While the above description contains many specificities, these should be not construed as limitations on the scope of the invention, but as exemplification of the presently-preferred embodiments thereof. Many other ramifications are possible within the teaching to the invention. For example, the improved visor-type face shield for dentist can be successfully used in the other than dental medical fields, e.g. such as pediatrics, etc.

Thus, the scope of the invention should be determined by the appended claims and their legal equivalents, and not by examples given.

THE DRAWING REFERENCE NUMERALS

1.—a visor portion;
2.—a shield portion;

3.—a first pivotable connecting means;
4.—a second pivotable connecting means;
5.—a visor assembly;
6.—a visor member;
7.—a forehead member;
8.—a visor first extension;
9.—a visor second extension;
10.—a band;
11.—a band first connection means;
12.—a band second connection means;
13.—a first half of the first "Velcro" lock;
14.—a second half of the first "Velcro" lock;
15.—a first end of the band 10;
16.—a second end of the band 10;
17.—an outer side of the visor first extension 8;
18.—an inner side of the band's first end;
19.—a free end of the visor first extension;
20.—a first half of the second "Velcro" lock;
21.—a second half of the second "Velcro" lock;
22.—an outer side of the visor second extension 9;
23.—an inner side of the band's second end;
24.—a free end of the visor second extension;
25.—a face shielding means;
26.—a rest;
27.—a shield lower portion;
28.—a shield upper portion;
29.—a visor first connecting means;
30.—a visor second connecting means;
31—a shield first connecting means;
32.—a shield second connecting means;
33.—a face shield;
34.—an inner side of the face shield 33;
35.—horizontal axis;
36.—an upper surface of the visor member 6;
37.—a gap;
38.—a conventional ventilation direction;
39—39 is a cross-sectional view.

What is claimed is:

1. An improved visor-type face shield for dentist comprising
   a visor portion including
      a visor assembly comprising
         a visor member placed in a lateral plane, and
         a forehead member placed in a longitudinal plane and coupled with said visor member;
      a visor first extension coupled with said visor assembly, and wherein said visor first extension includes a first extension free end;
      a visor second extension coupled with said visor assembly, and wherein said visor second extension includes a second extension free end;
      a band comprising a first free end and a second free end;
      a band first connection means attached to an outer side of said first extension free end;
      a band second connection means attached to an outer side of said second extension free end, and wherein said first free end of said band is coupled with said first extension free end of said visor portion by said band first connection means, and said second free end of said band is coupled with said second extension free end of said visor portion by said band second connection means;
   a shield portion including
      a face shielding means comprising
         a face shield having a curved configuration and comprising
            at least one of a plurality of rests located in the middle area of said face shield along a horizontal axis and coupled with an inner surface of said face shield;
            a lower portion bent into direction of said visor portion, and
            an upper portion bent into direction of said visor portion;
      a first pivotable connecting means providing a rotation of said face shield around said horizontal axis and including
         a visor first connecting means rigidly connected to said visor portion, and
         a shield first connecting means rigidly connected to said face shielding means;
      a second pivotable connecting means providing said rotation of said face shield around said horizontal axis and including
         a visor second connecting means rigidly connected to said visor portion, and
         a shield second connecting means rigidly connected to said face shielding means, and wherein said visor first connecting means is coupled with said shield first connecting means, and said visor second connecting means is coupled with said shield second connecting means.

2. The face shield of claim 1, wherein further said a first pivotable connecting means and said second pivotable connecting means are non-pivotable.

3. The face shield of claim 1, wherein further said at least one of said plurality of said rests is extended from said face shield.

4. The face shield of claim 1, wherein further said visor first extension and visor second extension are appropriately extended from said visor assembly.

5. The face shield of claim 1, wherein further said band is flexible.

6. The face shield of claim 1, wherein further said shield portion is coupled with said visor portion in the manner providing a gap between said inner surface of said face shield and said visor member.

7. The face shield of claim 1, wherein further said band first connection means is presented by a first hook and loop tape lock, wherein a first half of said first hook and loop tape lock is appropriately attached to an outer side of said visor first extension at its free end, and a second half of said first hook and loop tape lock is appropriately attached to an inner side of said first free end of said band, and wherein further said band second connection means is presented by a second hook and loop tape lock, and a first half of a second hook and loop tape lock is appropriately attached to an outer side of said visor second extension at its free end, and a second half of said second hook and loop tape lock is appropriately attached to an inner side of said second free end of said band.

8. The face shield of claim 7, wherein the connection of said a first half of said first hook and loop tape lock to said outer side of said visor first extension and the connection of said first half of said second hook and loop tape lock to said outer side of said visor second are provided by a double side adhesive tape.

* * * * *